United States Patent [19]

Taelman

[11] 4,291,685
[45] Sep. 29, 1981

[54] THERAPEUTIC HEAT AND COSMETIC APPLICATOR

[76] Inventor: Dennis L. Taelman, 6200 S. 30th St., Phoenix, Ariz. 85040

[21] Appl. No.: 49,041

[22] Filed: Jun. 15, 1979

[51] Int. Cl.³ .................. A61H 1/00; A61H 23/02
[52] U.S. Cl. ............................. 128/24.1; 128/399; 128/32
[58] Field of Search .............. 128/24.1, 32, 67, 254, 128/260, 261, 399, 400

[56] References Cited

U.S. PATENT DOCUMENTS

| | | | |
|---|---|---|---|
| 1,952,659 | 3/1934 | Dorrance | 128/399 |
| 1,974,031 | 9/1934 | Merrill | 128/24.1 |
| 2,385,501 | 9/1945 | Fevas | 128/24.1 |
| 2,488,591 | 11/1949 | Fevas | 128/24.1 |
| 3,903,888 | 9/1975 | Buelow et al. | 128/260 |
| 3,924,335 | 12/1975 | Balamuth | 128/24 A |
| 4,215,476 | 8/1980 | Armstrong | 128/276 |

FOREIGN PATENT DOCUMENTS

| | | | |
|---|---|---|---|
| 68685 | 3/1949 | Denmark | 128/24.1 |
| 735366 | 8/1955 | United Kingdom | 128/32 |

Primary Examiner—Stephen C. Pellegrino
Attorney, Agent, or Firm—Warren F. B. Lindsley

[57] ABSTRACT

A cosmetic applicator for applying heat and medicament, unguents, cosmetics and the like to the face or other parts of the body.

4 Claims, 14 Drawing Figures

U.S. Patent  Sep. 29, 1981  Sheet 1 of 2  4,291,685
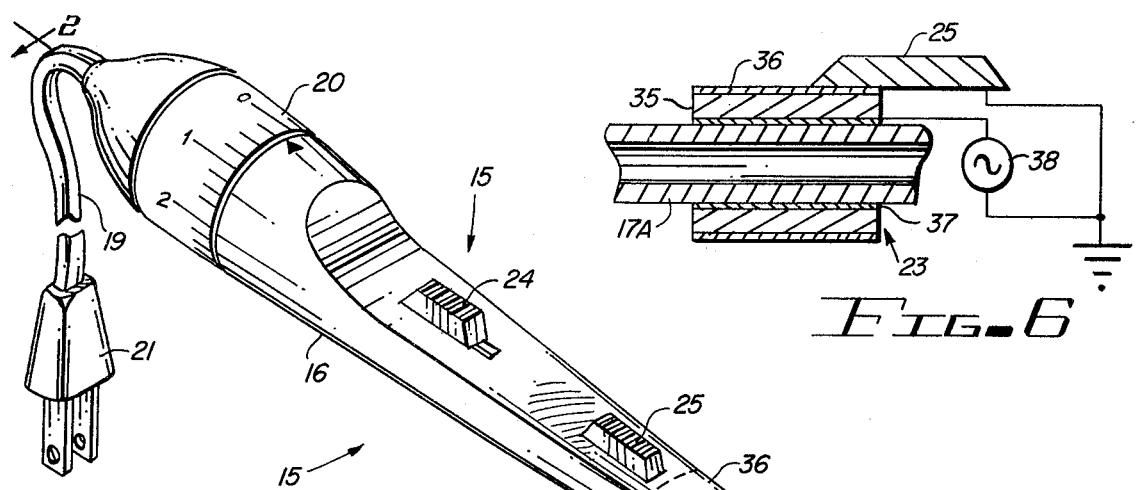
FIG. 1
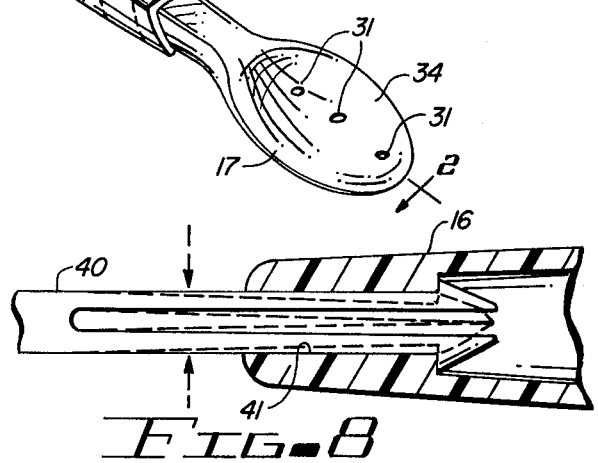
FIG. 6
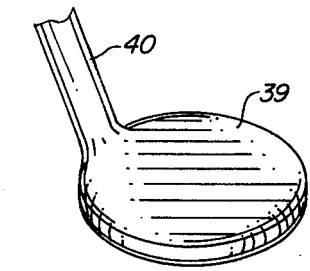
FIG. 7
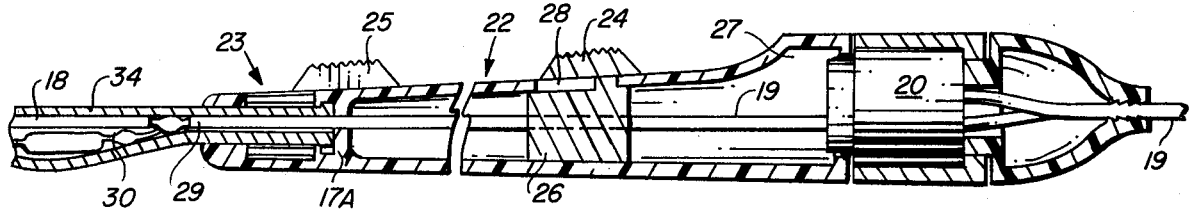
FIG. 8
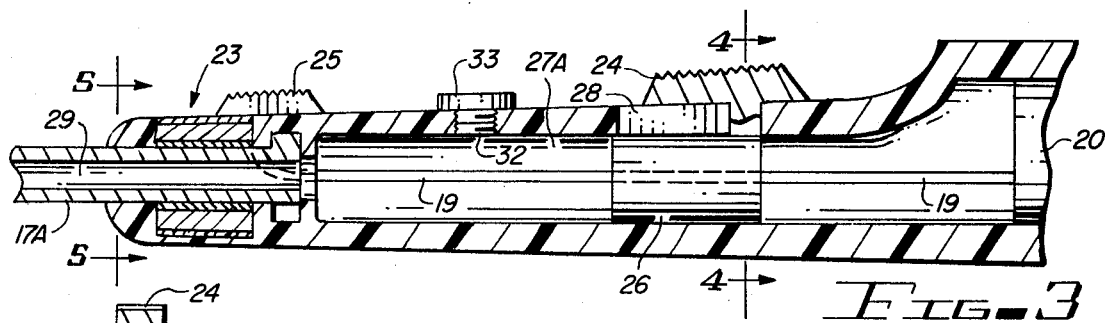
FIG. 2
FIG. 3
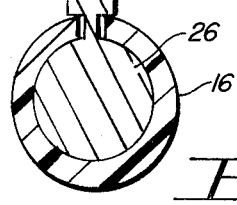
FIG. 4
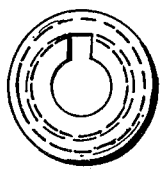
FIG. 5

THERAPEUTIC HEAT AND COSMETIC APPLICATOR

BACKGROUND OF THE INVENTION

This invention relates to a convenient hand-held facial heat applicator which is adaptable to apply medicaments, unguents, cosmetics and the like to the face and other parts of the body.

After years of encouraging women to cover their skin with layers of makeup, the trend now is to place more emphasis on the skin itself. The care of the skin, particularly cleaning and lubricating, is a fast growing segment of the cosmetic business. The jar of cold cream is now being replaced with products to firm up wrinkled necks and nourish the skin.

Beauty clinics cater to men and women who want treatments that they hope will keep their skin appearing young, smooth and wrinkle free. A cosmetologist cleans the skin with unscented makeup remover and lotions. Then a lubricant is applied with a small hot iron to soften the pores. This face ironing is followed by a herbal or seaweed steam facial, manual and deep-pore cleaning and further make up consultation and application is then undertaken.

In essence, most beauty parlors clean the skin thoroughly.

A convenient hand-held home and business appliance is needed for applying heat to the face or body which in one form may also include a vibrator and in another form a medicament dispenser. A compreshensive device will include the heating iron, vibrator and medicament dispenser all in one appliance the functions of which may be used individually or in combination.

DESCRIPTION OF THE PRIOR ART

U.S. Pat. No. 1,573,693 discloses an electric facial device having a curved body portion constructed of absorbing material and including an electric heating coil therein.

U.S. Pat. No. 1,653,901 discloses a hand-held therapeutical heating and steaming instrument for applying heat to the face or body of a person with an electrical heater within a relatively small hollow body supported by a handle. An absorbent pad is detachably secured to the heating body continguous to the electric heater. The pad may be dipped or immersed in a liquid.

U.S. Pat. No. 1,714,693 discloses a facial heat applicator employing a relatively thick hollow disc-like head having a rigid front wall to the heated and an electrical resistance element disposed in the head at the inner side of the front wall.

U.S. Pat. No. 1,952,659 discloses a cosmetic applicator for applying cosmetics and the like to the face and other parts of the body and employs a perforated face plate through which a medicament may seep out on to the face of the applicator.

U.S. Pat. No. 2,469,771 discloses a facial hydrotherapeutic device for treating the slack flesh and skin adjacent the eyes first with warm or hot water and then cold water.

SUMMARY OF THE INVENTION

In accordance with the invention claimed, an improved therapeutic heat, vibration and cosmetic applicator is provided which makes it easier and more convenient to apply heat, vibration and cosmetics to selected portions of the face and other portions of the body.

It is, therefore, one object of this invention to provide a new and improved heating appliance for the treatment of the skin of the face of a person and is especially designed for home and beauty parlor use.

Another object of this invention is to provide a new and improved facial therapeutic device which may be selectively used for heating, vibrating and the application of cosmetics to chosen portions of the skin.

A further object of this invention is to provide a new and improved hand-held facial skin treatment applicator which can sequentially heat, vibrate and then apply cosmetics to selected portions of the facial skin by the user.

A still further object of this invention is to provide a new and improved facial applicator that contains within a comparatively small hand-held implement a heating element and if so desired a vibrator and medicant which is heated before application to the face of a user.

A still further object of this invention is to provide a new and improved hand-held therapeutic cosmetic skin treatment device which may be used by beauty operators as well as for individual home use.

A still further object of this invention is to provide a new and improved relatively small hand held device which may be used to provide heat and vibration treatments to selected parts of the body.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWINGS

FIG. 1 is a perspective view of a hand-held therapeutic heat vibrator and cosmetic applicator and embodying the invention;

FIG. 2 is a cross-sectional view of FIG. 1 taken along the line 2—2;

FIG. 3 is a partial enlarged view similar to FIG. 2 showing in more detail the cosmetic applicator feature of the hand-held applicator;

FIG. 4 is a cross-sectional view of FIG. 3 taken along the line 4—4;

FIG. 5 is cross-sectional view of FIG. 3 taken along the line 5—5;

FIG. 6 is a diagrammatic illustration of the vibrator feature of the applicator shown in FIG. 1;

FIG. 7 is a modification of the face engaging element shown in FIG. 1;

FIG. 8 is a partial view of a further modification of the fce engaging element illustrating one way of making it detachable with the housing of the applicator;

DESCRIPTION OF THE PREFERRED EMBODIMENT

Figure 9:
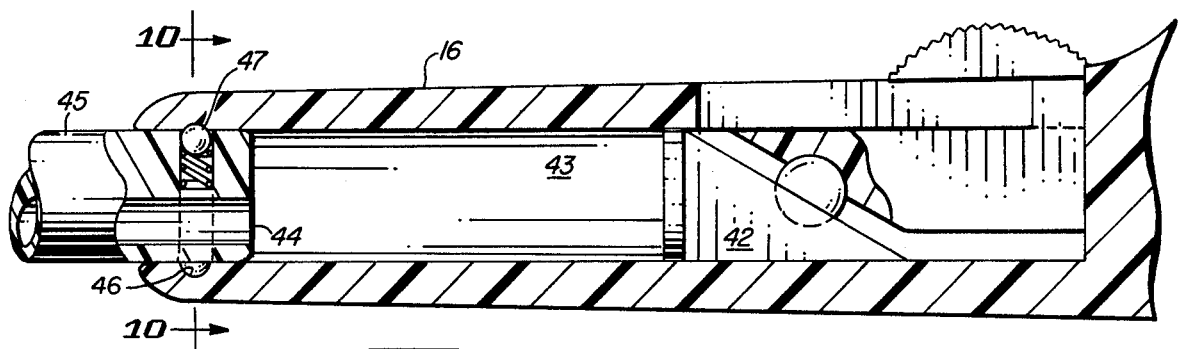
FIG. 9 is a modification of the applicator shown in FIG. 1 embodying a detachable face engaging element and front loading cream appalicator.

Referring more particularly to the drawing by characters of reference, FIGS. 1-6 discloses an electric heating device 15 for facial or other body skin treatment which comprises a tubular handle 16 provided at its outer end with a heating head or element 17 that contains an electric heat resistance element 18 associated with a source of electric energy through the medium of a cord 19 connected to a rheostat 20 and passing through the handle 16 to a plug 21 for connecting to a source of electric power.

As noted from FIGS. 1-6, the electric heating device 15 further comprises a medicament, unguent and cosmetic dispensing means 22 and vibrator means 23 controlled by actuating means 24 and 25, respectively. The dispensing means 22 may comprise a plunger 26 that is slidably moveable within the hollow interior 27 of the tubular handle 16. Plunger 26 is physically moved longitudinally of handle 16 by the user's movement of the actuating means 24 in a slot 28 in handle 16.

As shown in FIGS. 2 and 3, the hollow interior 27 in portion 27A of the tubular handle 16 is filled with a suitable medicament, unguent or cosmetic which is selectively pushed and moved by the plunger 26 through a passageway 29 into the hollow interior 30 of the heating head or element 17 where it is dispensed out of one or more openings 31.

It should be noted that the material pushed and dispensed out of openings 31 by plunger 26 may be inserted into portion 27A of the hollow interior 27 of the handle through an opening 32 in handle 16 closed by a cap or plug 33 or through the front end of the handle of the device as shown in FIG. 9.

Although the heating head or element 17 may be of any suitable configuration, a spoon shaped hollow configuration has been found to be a satisfactory configuration with the opening of the normal spoon filled in to form a flat plane surface 34. Since the material dispersed through openings 31 by plunger 26 passes through the hollow interior of the heating element this material is heated by the heating element 17 before reaching the skin of the user.

FIGS. 1, 2, 3 and 6 further illustrate that the heating device comprises the vibrator means 23. This means may comprise a piezoelectric type of device which is diagrammatically shown as comprising a piezoelectric transducer sleeve like device 35 formed around handle 16, as shown and having a metal ground electrode 36 and a metal back electrode 37 interconnected by the on-off actuating means 25 to a source of high frequency source of power 38 such as frequencies above 100MH$_z$.

It should be noted that the mode of vibration of a transducer is determined by its crystallographic orientation, the geometry and the direction of the applied field, the operating frequency of which is determined by the transducer thickness. Other types of transducer material may also be used for high frequency transducer action.

Since the heating head is inserted into the hollow interior of the transducers device the shank 17A of the heating element 17 must be in snug relationship with the transducer to serve as the proagation medium so as to vibrate when the vibrator means 23 is actuated. FIGS. 7 and 8 illustrate two modifications of the heating head shown in FIG. 1 wherein FIG. 7 discloses that the head 39 may be flat and arranged to extend laterally of the longitudinal axis of the tubular handle 16 and it or any other head configuration may have bifurcated stem 40 which may be flexed to be detachably inserted into the open end 41 of the tubular handle 16 and interlocked therewith as shown.

Figure 10:
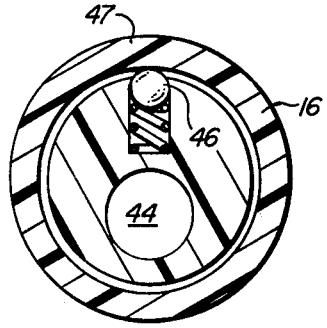
FIG. 10 is a cross-sectional view of FIG. 9 taken along the line 10—10.

FIGS. 9 and 10 illustrate a modification of the heating device 15 shown in FIGS. 1-6 wherein the cosmetic dispensing means 22 comprises a plunger 42 that forces cream or other suitable material 43 through opening 44 in the heating element 45. As shown, the heating element 45 comprises a ball bearing arrangement 47 that detachably interconnects with an indentation 46 in the periphery of the hollow interior of the tubular handle 16.

Figure 12:
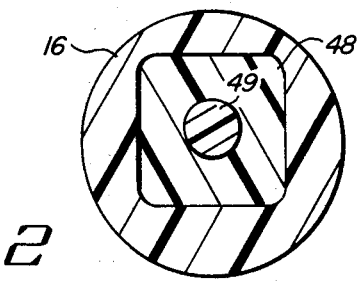
FIG. 12 is a cross-sectional view of FIG. 11 taken along the line 12—12.
Figure 11:
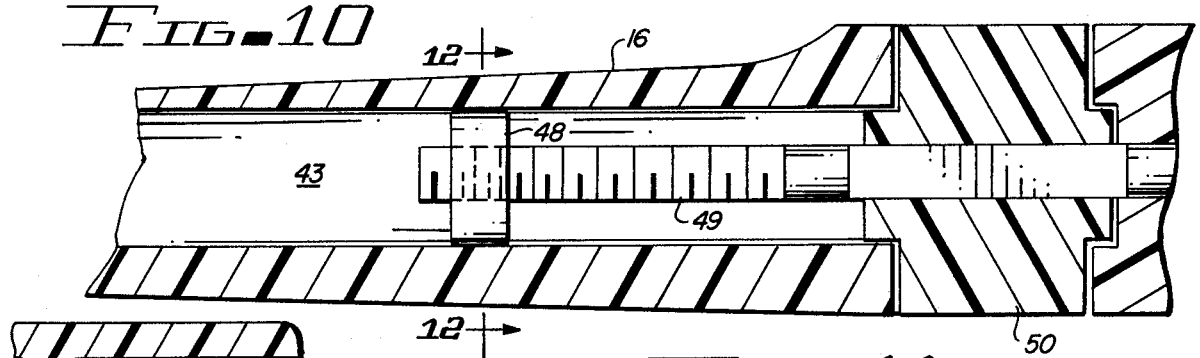
FIG. 11 illustrates a partial view of a further modification of the medicant applicator shown in FIGS. 1 and 9.

FIGS. 11 and 12 illustrate a further means of dispensing medicaments, unguents, cosmetics and other similar material from the tubular handle 16 by means of a plunger 48 threadedly mounted on a bolt 49 which is turned by a rotatable collar 50 journaled in the hollow interior of handle 16.

Figure 14:
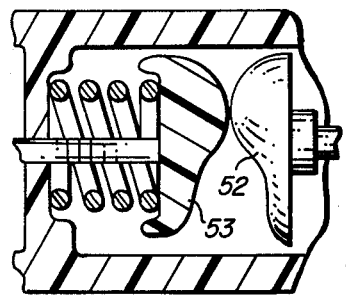
FIG. 14 is a partial cross-sectional view illustrating the mechanical vibratory element shown in FIG. 13 in a different position.
Figure 13:
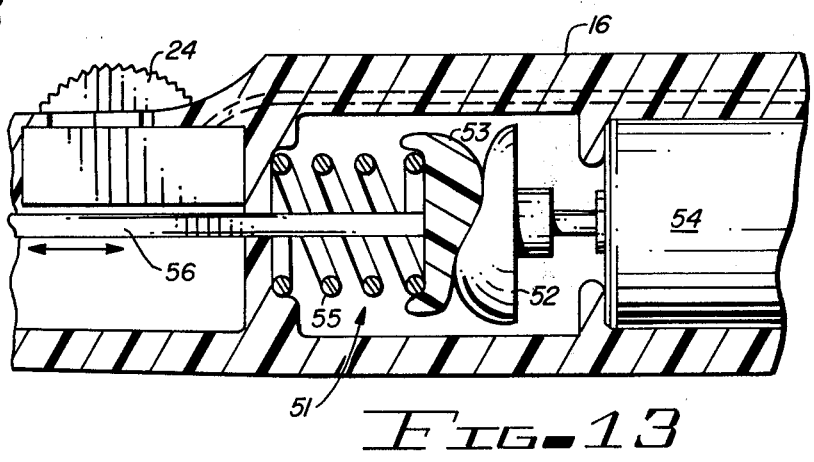
FIG. 13 is a partial cross-sectional view of a modification of the vibratory shown in FIGS. 1 and 6.

FIGS. 13 and 14 illustrate a modification of the vibrator means 23 shown in FIGS. 1, 2, 3 and 6 wherein a mechanical mechanism 51 is shown. This mechanism comprises a pair of cam surfaces 52 and 53 which are rotated relative to each other by a motor 54. The motor is controlled by the actuating means 24. As shown cam surface 53 is biased into engagement by a spring 55 and the longitudinal movement of shaft 56 connected to the heating head due to the rotation of cam surface 52 causes vibratory action thereof in a known manner.

Thus, in accordance with the invention claimed a new and improved therapeutic heat, vibrator and cosmetic applicator is provided which may provide one or more functions simultaneously and in any selected sequence for improved skin care and treatment.

Although but a few embodiments of the invention have been shown and claimed, it will be apparent to those skilled in the art that various changes and modifications may be made therein without departing from the spirit of the invention or from the scope of the appended claims.

What is claimed is:

1. A therapeutic hand-held electrical applicator for facial treatment comprising:
    a hollow elongated tubular handle,
    a hollow heat applying element mounted at one end of said handle,
    an electrical means comprising a rheostat mounted within said handle and a heating means mounted within said element,
    said rheostat selectively controlling the electric current flowing through said heating means for heating said element,
    a material dispensing means mounted within said handle,
    at least one opening in said element,
    conduit means connecting said material dispensing means with said opening, and
    control means on the exterior of said handle for selectively controlling said electrical means and said material dispensing means,
    said control means comprising a sleeve mounted for rotatable movement around the outer periphery of said handle for controlling said rheostat and a switch for selectively actuating said material dispensing means, a vibrator means mounted within said handle for vibrating said heat applying element, said vibrator means comprising a piezoelectric transducer having a sleeve mounted around the outer periphery of said handle adjacent said heat applying element; and said control means actuating said vibrator means.

2. The therapeutic hand-held electrical applicator set forth in claim 1 wherein:

said control means further comprises another switch mounted on the outer periphery of said handle for selectively actuating said vibrator means.

3. The therapeutic hand-held electrical applicator set forth in claim 1 wherein:

said heat applying element comprises a hollow spoon-like member having a flat surface covering its concave opening.

4. The therapeutic hand-held electrical applicator set forth in claim 1 wherein:

said handle comprises a tapered configuration having its narrow portion at said one end and its hand engaging portion at its other end, and said sleeve being formed around said other end.

* * * * *